US00PP33757P3

(12) United States Plant Patent
McLean

(10) Patent No.: US PP33,757 P3
(45) Date of Patent: Dec. 21, 2021

(54) APPLE TREE NAMED 'MC-51'

(50) Latin Name: ***Malus domestica* Borkh.**
Varietal Denomination: MC-51

(71) Applicant: AD McLean Investments Pty Ltd, Axedale (AU)

(72) Inventor: Allan McLean, Axedale (AU)

(73) Assignee: A D MCLEAN INVESTMENTS PTY LTD, Axedale (AU)

( * ) Notice: Subject to any disclaimer, the term of this patent is extended or adjusted under 35 U.S.C. 154(b) by 0 days.

(21) Appl. No.: 16/501,519

(22) Filed: Apr. 22, 2019

(65) Prior Publication Data

US 2020/0022293 P1 Jan. 16, 2020

Related U.S. Application Data

(60) Provisional application No. 62/764,080, filed on Jul. 16, 2018.

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418
See application file for complete search history.

(56) References Cited

FOREIGN PATENT DOCUMENTS

AU 00201532 6 * 1/2016 ..... A01H 6/7418

OTHER PUBLICATIONS

UPOV hit on an Apple tree named, 'MC-51', AI PBR 20155326, filed Dec. 2, 2015.*
UPOV hit on Apple tree named, 'MC-51', AU PBR 2015326, Dec. 2, 2015.*

* cited by examiner

*Primary Examiner* — Anne Marie Grunberg
(74) *Attorney, Agent, or Firm* — Michelle Bos Legal LLC

(57) ABSTRACT

'MC-51' is a whole tree mutation of the 'MC38' variety of apple tree, characterized by the early and homogeneous coloration of its fruit.

5 Drawing Sheets

Latin name: *Malus domestica* Borkh.
Variety denomination: 'MC-51'.

BACKGROUND OF THE VARIETY

'MC-51' is a new and distinct variety of apple tree *Malus domestica* Borkh. This new variety is a whole tree mutation of the 'MC38' apple tree variety (U.S. Plant Pat. No. 16,654), characterized by the early and homogeneous coloration of its fruit. 'MC-51' was first observed by the inventor in a commercial apple orchard at Sutton Grange, Victoria, Australia in 2008. The variety was asexually reproduced by chip budding in 2011 at Presina, Italy. Test trees grown at Cornaiano, Italy were observed to retain the characteristics of the original 'MC-51' tree. The new variety has since been asexually propagated through successive generations and has been observed to remain true to type.

BRIEF DESCRIPTION OF THE VARIETY

'MC-51' was first selected for the early and homogeneous coloration of its fruit, as compared to its parent 'MC38'. The early, even coloring reduces susceptibility to sunburn and allows the fruit to be harvested in one picking. Additional distinguishing characteristics are described in Table 1.

TABLE 1

Comparison of 'MC-51' to parent 'MC38'

| | MC38 | MC51 |
|---|---|---|
| Tree - bark color | Greyed-orange 177A | Greyed-green 197A |
| Leaf - petiole color | Greyed-red 179A | Yellow-green 145A |
| Fruit - stem color | Greyed-orange 176B | Grey-brown 199C |
| Fruit russet in stem cavity | Low | None |
| Fruit - uniformity of coloration | Starts and ends coloring with stripes | More narrow stripes start to color earlier, with color increasing to solid flush with no stripes |
| Fruit - color | Solid striped red 53A overcolor covering 80% of yellow-green 145A ground color | Early striping turns to solid flush red-purple 59A covering 90% of yellow-green 145A ground color |
| Fruit - date full color is achieved | Late (2 weeks before harvest) | Earlier (4 weeks before harvest), reducing susceptibility to sunburn |
| Harvest - number of picks | 2 | Usually only 1 due to homogeneous coloring |
| Harvest yield | | |

'MC-51' is distinguished from similar varieties 'Rosy Glow' (not patented) and 'Cripps Pink' (U.S. Plant Pat. No. 7,880), as set forth in Table 2 below.

TABLE 2

Comparison of 'MC-51' to parent 'Rosy Glow' and 'Cripps Pink'

| Comparator | Characteristic | Expression of Comparator | Expression of 'MC51' |
|---|---|---|---|
| 'Rosy Glow' | Intensity of fruit overcolor | Medium/High | High |
| 'Rosy Glow' | Tree habit | Upright | Spreading to drooping |
| 'Cripps Pink' | Extent of overcolor | Small | Very large |

BRIEF DESCRIPTION OF THE PHOTOGRAPHS

DETAILED BOTANICAL DESCRIPTION OF THE VARIETY

Figure 1:
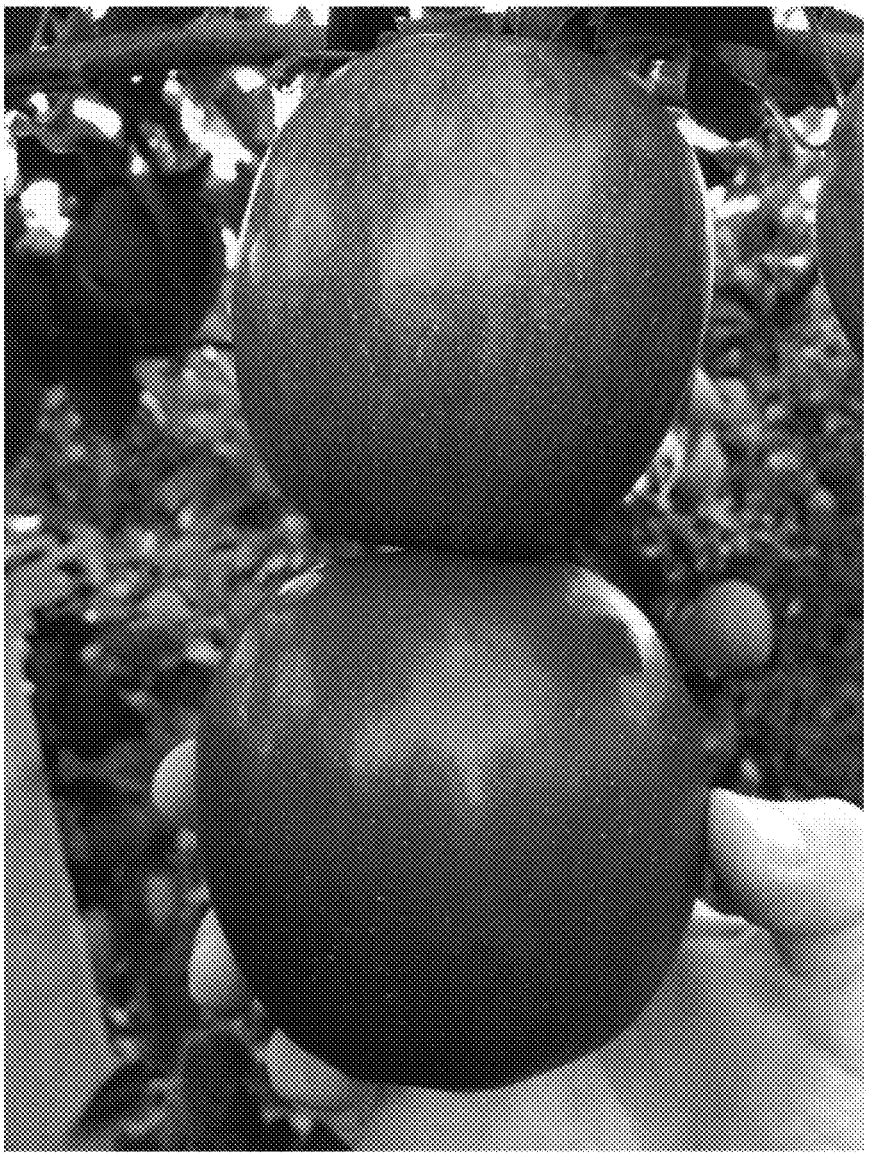
FIG. 1 shows the even coloration of fruit of 'MC-51' (bottom) compared to parent variety 'MC38' (top)
Figure 2:
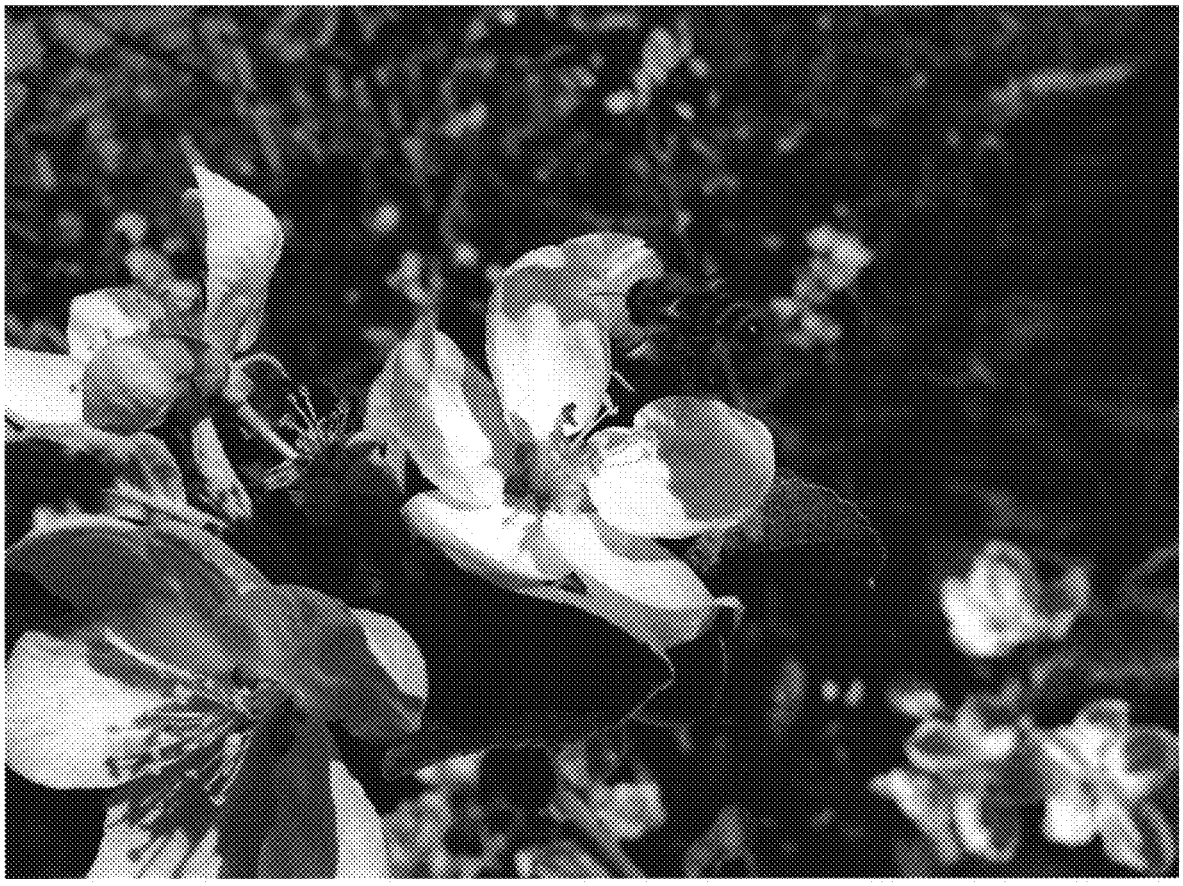
FIG. 2 shows blossoms of 'MC-51'.
Figure 3:
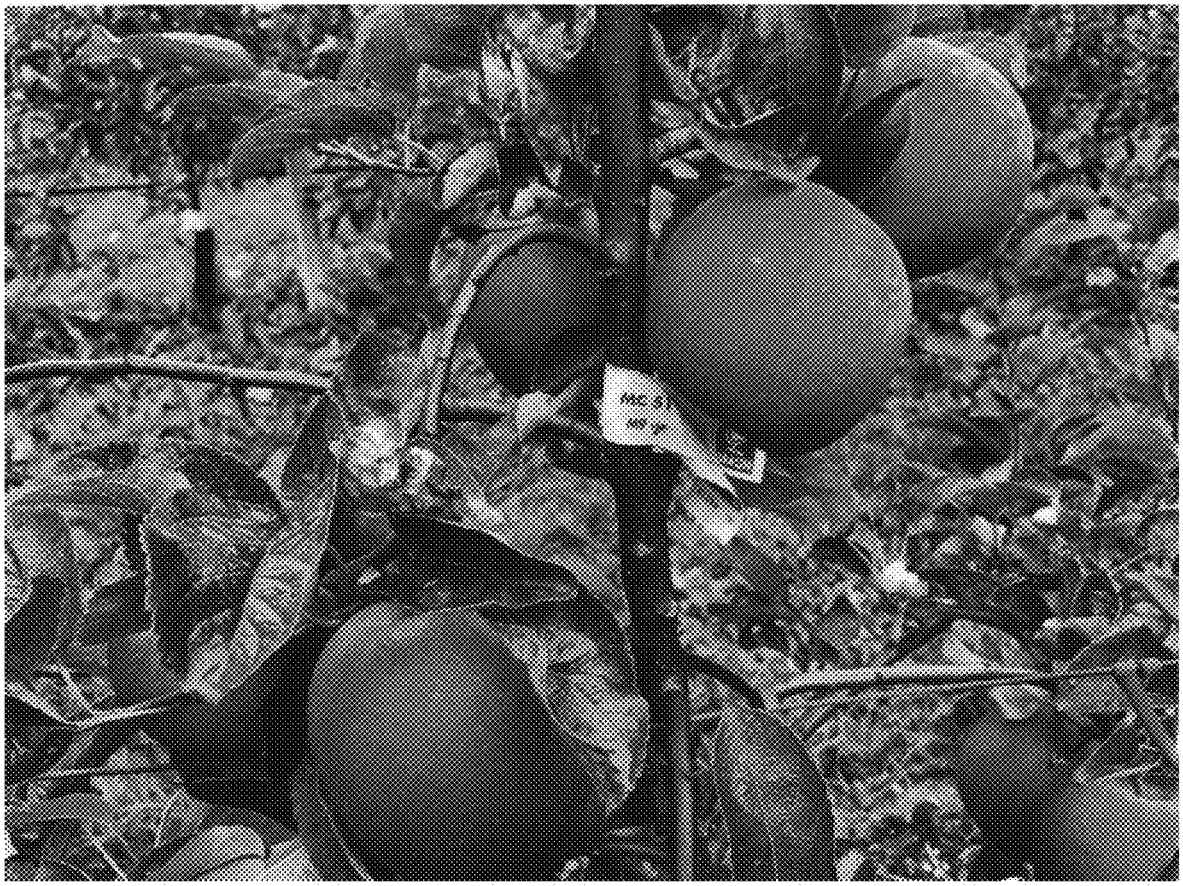
FIG. 3 shows fruit and leaves of 'MC-51'.
Figure 4:
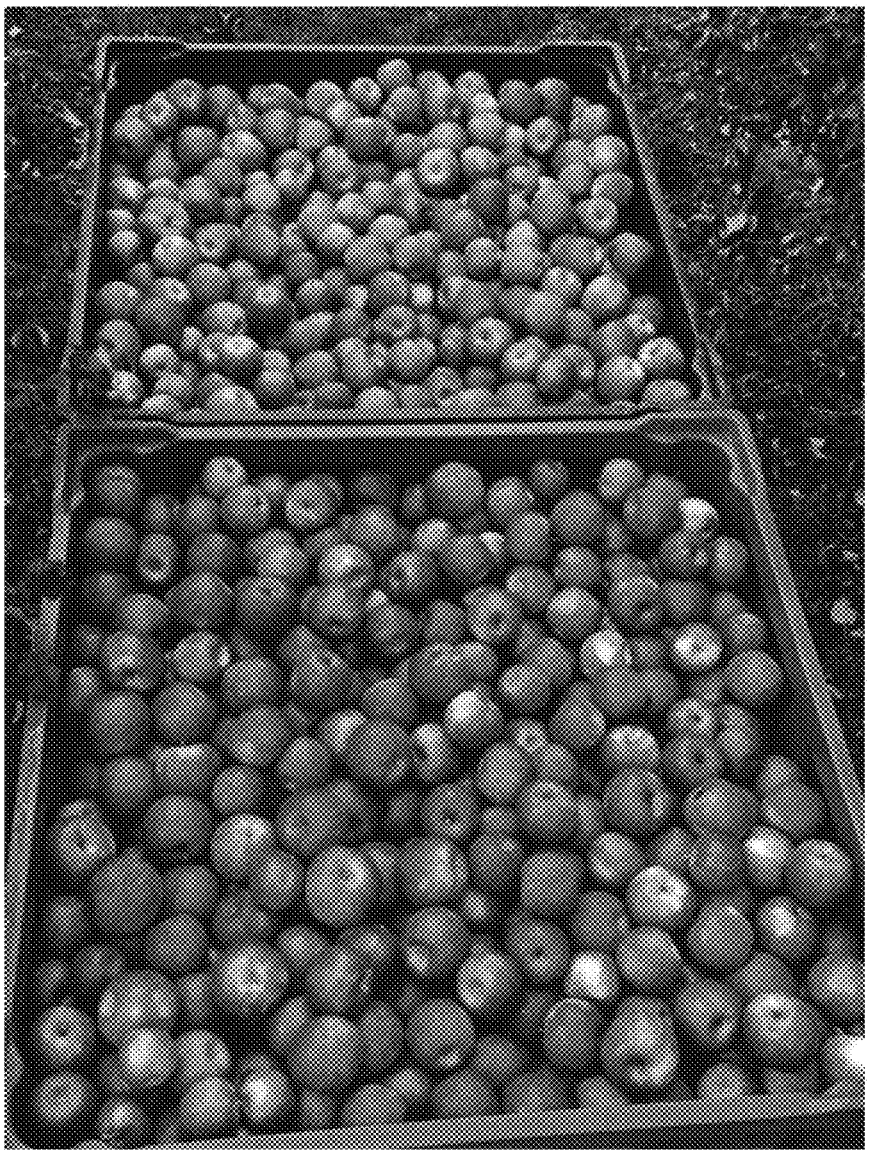
FIG. 4 shows the even coloration of a bin of fruit of 'MC-51' (bottom) compared to parent variety 'MC38' (top)
Figure 5:
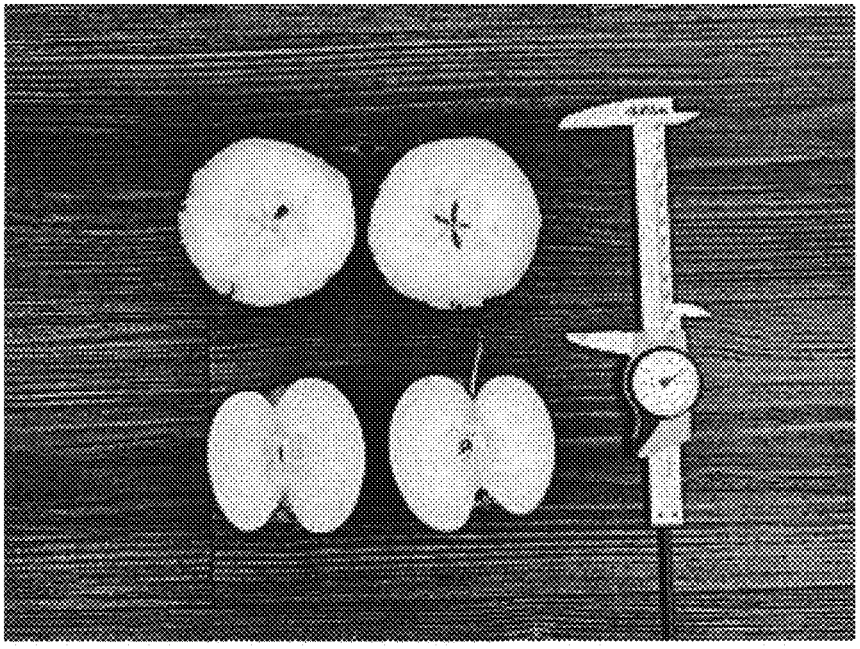
FIG. 5 shows sectioned fruit of 'MC-51'.

The following-detailed botanical description is based on observations made during the 2015 through 2017 growing seasons at Cornaiano, Italy of trees grown on 'M9' T337 virus-free rootstock (not patented) and planted in 2013. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor*.—Medium.
*Type*.—Ramified.
*Habit*.—Spreading to drooping.
*Bearing*.—On spurs and long shoots.
*Height*.—Apical dominant; dependent on pruning.
*Trunk diameter* (*at* 30 *cm above the graft*).—2.9 cm.
*Bark texture*.—Smooth.
*Bark color*.—Greyed-green 197A.
*Trunk lenticel shape*.—Oval.
*Trunk lenticel density*.—4 to 5 per $cm^2$.
*Trunk lenticel color*.—Greyed yellow 151A.

Branch (fruiting branches located at around 1 m above the graft union):

*Length*.—Up to 80 cm; dependent on pruning.
*Diameter*.—14 mm at 5 cm from trunk.
*Crotch angle*.—70 to 80 degrees.
*Bark color*.—Grey purple 166A.
*Lenticel length*.—1 mm to 1.5 mm.
*Lenticel shape*.—Oblong.
*Lenticel density*.—4 to 5 per $cm^2$.
*Lenticel color*.—Greyed-yellow 161A.

One year old shoot:

*Length*.—10 to 30 cm.
*Color*.—Greyed-purple 187A.
*Pubescence*.—Absent.
*Thickness*.—6 mm to 10 mm at 5 cm from trunk.
*Position of vegetative bud relative to shoot*.—Outward.
*Shape of vegetative bud apex*.—Pointed.
*Vegetative bud color*.—Greyed-yellow 166A.
*Internode length*.—20 mm to 35 mm.
*Growth pattern*.—Straight.
*Lenticel density*.—4 to 5 per $cm^2$.

Flower buds:

*Quantity per spur*.—6.
*Shape*.—Oval.
*Length*.—10 mm.
*Diameter*.—8.5 mm.
*Color of closed bud*.—Greyed-purple N187A.
*Color of bud at balloon stage*.—Red 47B.

Flowers:

*Inflorescence type*.—Umbellate.
*Diameter of fully open flower*.—5 cm.
*Flower depth*.—Shallow.
*Relative position of petal margin*.—Not touching.
*Number per cluster*.—6 plus king flower.
*Date of first bloom*.—April 12 (2 days after 'Gala').
*Date of full bloom*.—April 19.
*Pollination requirement*.—Required; 'Gala' or 'Granny Smith'.

Petals (measured on king flower):

*Number per flower*.—5.
*Shape*.—Oval to oblong.
*Length*.—1.6 cm.
*Width*.—1.2 cm.
*Apex*.—Round.
*Base*.—Slightly acuminate.
*Margin*.—Smooth, unruffled.
*Vein prominence*.—Smooth to rugulose.
*Color of upper surface*.—Red-purple 66C.
*Color of lower surface*.—Red-purple 66C.
*Color of veins*.—Red-purple N66B.

Stigma:

*Position*.—Above anthers.
*Color*.—White 155D.

Style:

*Length*.—10 mm.
*Color*.—Yellow-green 154D.

Ovary:

*Length*.—5 mm.
*Color*.—Yellow-green 144A.

Anthers:

*Quantity*.—10 (+/−2).
*Length*.—7 mm.
*Color*.—Yellow-white 158B.
*Pollen color*.—Yellow-white 158B.

Pedicel:

*Length*.—2.0 cm.
*Diameter*.—0.13 cm.
*Color*.—Green 138D.

Sepals:

*Quantity*.—5.
*Color*.—Green 141D with red-purple 59A tip.
*Shape*.—Pointed.
*Margin*.—Smooth.

Leaves:

*Shape*.—Oval.
*Length*.—Up to about 65 mm.
*Width*.—Up to about 45 mm.
*Blade margin*.—Serrate, not undulating.
*Apex*.—Acute.

*Base shape*.—Cuneate.
*Profile in cross-section*.—Slighly concave.
*Pubescence of lower surface*.—Low.
*Color of upper surface*.—Green 139A.
*Color of lower surface*.—Yellow-green 147C.
*Color of vein*.—Green-white 157A.
*Color of expanding leaf blade*.—Green 139A.
*Attitude in relation to shoot*.—Outward.

Petiole:
*Length*.—24 mm.
*Diameter*.—1.2 mm.
*Color*.—Greyed-red 179A at attachment to shoot, fading to yellow-green 145A at leaf base.
*Stipules*.—About 2 present; length 1 to 2 mm.
*Stipule color*.—Greyed-red 179A.

Fruit:
*Quantity per cluster*.—Up to 3.
*Diameter*.—80 mm.
*Weight*.—230 g.
*Ratio of height to width*.—1 to 1.
*General shape in profile*.—Spherical, symmetrical.
*Position of maximum diameter*.—Upper 50% in profile.
*Ribbing*.—None.
*Crowning at calyx end*.—None.
*Depth of eye basin*.—Small, 7 to 10 mm deep.
*Width of eye basin*.—3 cm.
*Aperture of eye*.—Closed.
*Bloom of skin*.—Absent.
*Greasiness of skin*.—Absent.
*Anthocyanin coloration on young fruit*.—Present, red-purple 59A.
*Background color of skin*.—Yellow-green 145A.
*Amount of over color*.—90%.
*Over color of skin*.—Red-purple 59A.
*Intensity of over color*.—High.
*Pattern of over color*.—Solid flush.
*Amount of russet around stalk cavity*.—Absent.
*Amount of russet on cheeks*.—Absent.
*Area of russet around eye basin*.—Absent.
*Lenticel size*.—Large, up to 3 mm.
*Lenticel color*.—Yellow-orange 18C.
*Lenticel density*.—5 per $cm^2$ (+/−2).
*Length of stalk*.—2.5 cm (+/−0.7 cm).
*Thickness of stalk*.—2.5 mm.
*Depth of stalk cavity*.—1.2 cm to 2.2 cm.
*Width of stalk cavity*.—2.8 cm (+/−0.4 cm).
*Firmness of flesh*.—Medium; 6.5 kg per $cm^2$.
*Flesh texture*.—Crunchy.
*Aroma*.—Sweet with acidity; balanced.
*Juiciness*.—Medium.
*Brix*.—12° to 15° Brix.
*Flesh color*.—White 155A.
*Locule quantity*.—5.
*Aperture of locules*.—Open.
*Skin texture*.—Thick; glossy when polished.

Seeds:
*Quantity per fruit*.—Up to 2 per chamber; up to 10 total.
*Length*.—8 mm.
*Width*.—5 mm.
*Shape*.—Pointed.
*Color*.—Greyed-orange 175A.

Harvest:
*Time for harvest*.—End of October.
*Number of picks*.—Usually 1; no more than 2.
*Amount of fruit produced per tree per harvest*.—20 kg.

Disease resistance/susceptibility: Susceptible to black spot; Moderately tolerant to powdery mildew; Tolerant to scab.
Storage: Up to 12 months after harvest in CA storage.
Market use: Fresh.

The invention claimed is:

1. A new and distinct apple tree substantially as described and illustrated herein.

* * * * *